(12) United States Patent
Lysen et al.

(10) Patent No.: US 8,841,902 B2
(45) Date of Patent: Sep. 23, 2014

(54) TESTING DEVICE AND TESTING METHOD FOR NON DESTRUCTIVE DETECTION OF A DEFECT IN A TEST PIECE BY MEANS OF AN EDDY CURRENT

(75) Inventors: Heinrich Lysen, Garching (DE); Werner Bräu, Ismaning (DE)

(73) Assignee: Prüftechnik Dieter Busch AG, Ismaning (DE)

( * ) Notice: Subject to any disclaimer, the term of this patent is extended or adjusted under 35 U.S.C. 154(b) by 134 days.

(21) Appl. No.: 13/548,921

(22) Filed: Jul. 13, 2012

(65) Prior Publication Data

US 2013/0187643 A1   Jul. 25, 2013

Related U.S. Application Data

(60) Provisional application No. 61/588,730, filed on Jan. 20, 2012.

(51) Int. Cl.
*G01N 27/82* (2006.01)
*G01N 27/90* (2006.01)

(52) U.S. Cl.
CPC .................................. *G01N 27/9046* (2013.01)
USPC ............................................. 324/238; 702/35

(58) Field of Classification Search
CPC ..... G01B 7/06; G01N 27/90; G01N 27/9046; G01N 27/9073; G01N 27/9086; G01N 27/82; G01N 27/9006; G01N 27/9013
USPC ......................................... 324/238, 236, 240
See application file for complete search history.

(56) References Cited

U.S. PATENT DOCUMENTS

| | | | |
|---|---|---|---|
| 5,811,682 A * | 9/1998 | Ohtani et al. | 73/643 |
| 7,423,424 B2 | 9/2008 | Hoelzl et al. | |
| 7,443,156 B2 | 10/2008 | Hoelzl et al. | |
| 7,757,557 B2 * | 7/2010 | Thomas et al. | 73/602 |
| 2004/0066189 A1 | 4/2004 | Lopez | |
| 2007/0080681 A1 | 4/2007 | Hoelzl et al. | |
| 2008/0290866 A1 | 11/2008 | Cuffe et al. | |

FOREIGN PATENT DOCUMENTS

| | | |
|---|---|---|
| DE | 10 2004 051 506 A1 | 4/2006 |
| DE | 10 2012 100 460 A1 | 7/2013 |
| EP | 1 995 590 A1 | 11/2008 |
| EP | 1 794 582 B1 | 5/2009 |
| GB | 2 457 496 A | 8/2009 |
| JP | 05-292133 A | 11/1993 |
| JP | 2010-271317 A | 12/2010 |
| WO | 2006/007826 A1 | 1/2006 |

* cited by examiner

*Primary Examiner* — Harshad R Patel
*Assistant Examiner* — Roger Hernandez-Prewit
(74) *Attorney, Agent, or Firm* — Roberts Mlotkowski Safran & Cole, P.C.; David S. Safran (57) ABSTRACT

A test set-up (10) for non-destructive detection of a flaw in a device being tested by means of an eddy current has an excitation coil (14), to which an excitation signal (SE) can be sent to act on the device being tested (16) with an electromagnetic alternating field, a receiving coil (17) to generate a coil signal (SP), which is a function of the flaw in the device being tested (16), an analog-digital converter (21), which is coupled to the receiving coil (17) on the input side, a filter arrangement (22), which is coupled to the analog-digital converter (21) on the input side and is designed for band-pass filtering and scan rate reduction, and a demodulator (27), which is coupled to an output of the filter arrangement (22) on the input side.

11 Claims, 5 Drawing Sheets

FIG. 4A  Input Signal

FIG. 4B  Band Pass Filtering 2 × fa' and Scanning with fa' × 2

FIG. 4C  Scan Rate Reduction to fa" and Conversion to fm'

FIG. 4D  Demodulation, Low-Pass Filtering and Additional Scan Rate Reduction

TESTING DEVICE AND TESTING METHOD FOR NON DESTRUCTIVE DETECTION OF A DEFECT IN A TEST PIECE BY MEANS OF AN EDDY CURRENT

CROSS REFERENCE TO RELATED APPLICATION

This application is a conversion of provisional application 61/588,730 which was filed on Jan. 20, 2012.

BACKGROUND OF THE INVENTION

1. Field of the Invention

This application relates to a test set-up and a test method for non-destructive detection of a flaw in a device by means of an eddy current testing.

2. Description of Related Art

In a test set-up, an electromagnetic signal is produced in the device being tested that has an electrical conductivity. Eddy currents form in the device being tested and are picked up. Changes in these eddy currents around the flaw are analyzed.

International Patent Application Publication WO 2006/007826 A1 describes a device for non-destructive and contact-free detection of flaws in a device under test. In this case, a probe signal is scanned by means of an analog-digital-converter stage to form a demodulated digital measuring signal from the digitalized signal. The analog-digital-converter stage is triggered with a whole fraction of a frequency of a carrier oscillation.

UK Patent Application Publication GB 2 457 496 A deals with a system for detection of defects by means of eddy currents. A driver signal generates eddy currents in a test object. A measuring signal is digitalized by means of an analog-digital converter and then demodulated. Four or eight signal values are digitalized and demodulated per period of the measuring signal.

SUMMARY OF THE INVENTION

A primary object of this application is to provide a test set-up and a test method for non-destructive detection of a flaw in a device being tested by means of an eddy current, in which the accuracy of the analysis is increased.

This object is achieved with the test set-up and method described below.

In one embodiment, a test set-up for non-destructive detection of a flaw in a device being tested by means of an eddy current comprises an excitation coil, a receiving coil, an analog-digital converter, a filter arrangement, and a demodulator. An excitation signal can be sent to the excitation coil to act on the device being tested with an electromagnetic alternating field. The receiving coil is designed to generate a coil signal that is a function of the flaw in the device under test. The analog-digital converter is coupled to the receiving coil on the input side. The filter arrangement is coupled to the analog-digital converter on the input side and designed for band-pass filtering and scan frequency reduction. The demodulator is coupled to an output of the filter arrangement on the input side.

Filtering and demodulation advantageously take place digitally. Thus, analog components that are expensive in price are reduced. A value of a demodulator input signal that is sent to the demodulator is generated from several values of a converter output signal provided by an analog-digital converter. In this case, a converter scan frequency of the analog-digital converter can be set so high that the coil signal is overscanned. Thus, high accuracy in the detection of the coil signal is achieved. The accuracy is preserved by the band-pass filtering and scan frequency reduction so that a demodulator output signal is also determined very precisely at the output of the demodulator.

In one embodiment, the analog-digital converter is designed to provide the converter output signal with the converter scan frequency. The filter arrangement is designed to convert the converter output signal into the demodulator input signal with a reduced scan frequency. The reduced scan frequency is smaller than the converter scan frequency by a reduction factor of R. The demodulator is designed to demodulate the demodulator input signal. The reduction factor is preset. The reduction factor can be adjustable. Advantageously, a slow demodulator is adequate.

In one embodiment, the filter arrangement comprises a band-pass filter, which is coupled to the analog-digital converter on the input side and to the demodulator on the output side. The band-pass filter issues an input signal.

In one embodiment, the filter arrangement is designed to provide only one value as the demodulator input signal for the scan frequency reduction out of a first number P of values of the input signal. In this case, the first number P is an integer and is greater than or equal to 1. By the selection of the Pth value, an scan effective frequency reduction is achieved.

In one embodiment, the first number P is less than a reduction factor of R. The filter arrangement can be designed in multiple stages. At least two stages of the filter arrangement can be designed for scan frequency reduction. One stage of the filter arrangement can implement the selection of the Pth value.

In one embodiment, a scan frequency of the input signal is a rational multiple MIN of an excitation frequency of the excitation signal. The input signal has a first number M of values during a second number N of periods of the excitation signal. The first number M and the second number N are integers. The first number M and the second number N are usually different.

In one embodiment, the filter arrangement comprises an input filter, which is coupled to the band-pass filter on the input side and has the first number M of low-pass filter arrangements. The input filter in each case sends one of the first numbers M of values of the input signal to one of the first numbers M of the low-pass filter arrangements. The demodulator is coupled to an output of the input filter on the input side. Advantageously, a high flexibility is present in the analysis of the coil signal by the selection of the first number M and the second number N. The scan frequency of the input signal, which corresponds to the scan frequency of the demodulator, is limited upward. If for example, a higher value of the excitation frequency is selected, the rational ratio between the input signal and the excitation signal can be set in such a way that the input signal has only small values during a large number of periods of the excitation signal. If, however, the excitation frequency is set to a low value, the rational ratio can be set in such a way that the input signal has a high number of values during a few periods. As a result, the test set-up can be set in such a way that at any selected excitation frequency, as many values of the input signal per time unit as possible are analyzed. Since the scan frequency of the demodulator is the MIN-multiple of the excitation frequency, the demodulation can take place by changing a factor of MIN in various phase angles of the excitation signal. The analysis of the coil signal is thus not limited thereto so that it is performed only, for example, at 90° and 270° of the sinusoidal excitation signal. This results in high accuracy in the analysis of the coil signal.

Advantageously, the analog-digital converter, abbreviated AD converter, is implemented separately from the digital demodulator.

As a first number M and as a second number N, only integers that are free of a common whole factor, which is greater than 1, can be considered.

In one embodiment, the second number N is greater than 1. Thus, the analysis in the case of different phase angles of the excitation signal is carried out in two or more than two successive periods of the excitation signal.

In one embodiment, the first number M is greater than 1. Thus, at least two values in the second number N of periods of the excitation signal are analyzed.

The first number M can take on, for example, only odd numbers.

The excitation signal can be sinusoidal. Advantageously, the proportion of harmonic waves in the excitation signal is very low.

In one embodiment, a test method for non-destructive detection of a flaw in a device being tested by means of an eddy current comprises acting on the device being tested with an electromagnetic alternating field by means of an excitation coil. An excitation signal is sent to the excitation coil. Furthermore, a coil signal, which is a function of the flaw in the device under test, is generated by means of a receiving coil. A converter output signal is provided by digitalization of the coil signal. A demodulator input signal is generated by filtering the converter output signal with a band-pass filter characteristic as well as a scan frequency reduction. The demodulator input signal is demodulated by means of a demodulator.

Advantageously, the digitalization and the demodulation are performed at different rates. Thus, a high converter scan frequency can be achieved during digitalization, so that the Nyquist-Shannon sampling theorem can be maintained. By means of band-pass filtering and scan frequency reduction, a precise demodulator input signal can be generated. Thus, a high flexibility is provided to select the scan frequency corresponding to the excitation frequency. Consequently, a high accuracy can be achieved in the analysis of the coil signal. Advantageously, a further processing of the demodulator input signal is made possible with a slow-operating digital demodulator. Advantageously, a further processing of the demodulator input signal is made possible with a slow-operating digital demodulator In one embodiment, the test method comprises a digital demodulation with frequency conversion. The test method has a modulo demodulation.

In one embodiment, an analog-digital converter performs the digitalization in the converter scan frequency. The converter scan frequency can be at least twice the excitation frequency. Thus, the converter scan frequency can be set so high that an underscanning of the coil signal is avoided.

The invention is explained in more detail below based on the figures which show several embodiments and in which components, switch parts and operating blocks that are the same in function or action bear the same reference numbers and when components, switch parts and operating blocks correspond in their function, their description is not repeated.

DETAILED DESCRIPTION OF THE INVENTION

Figure 1A:
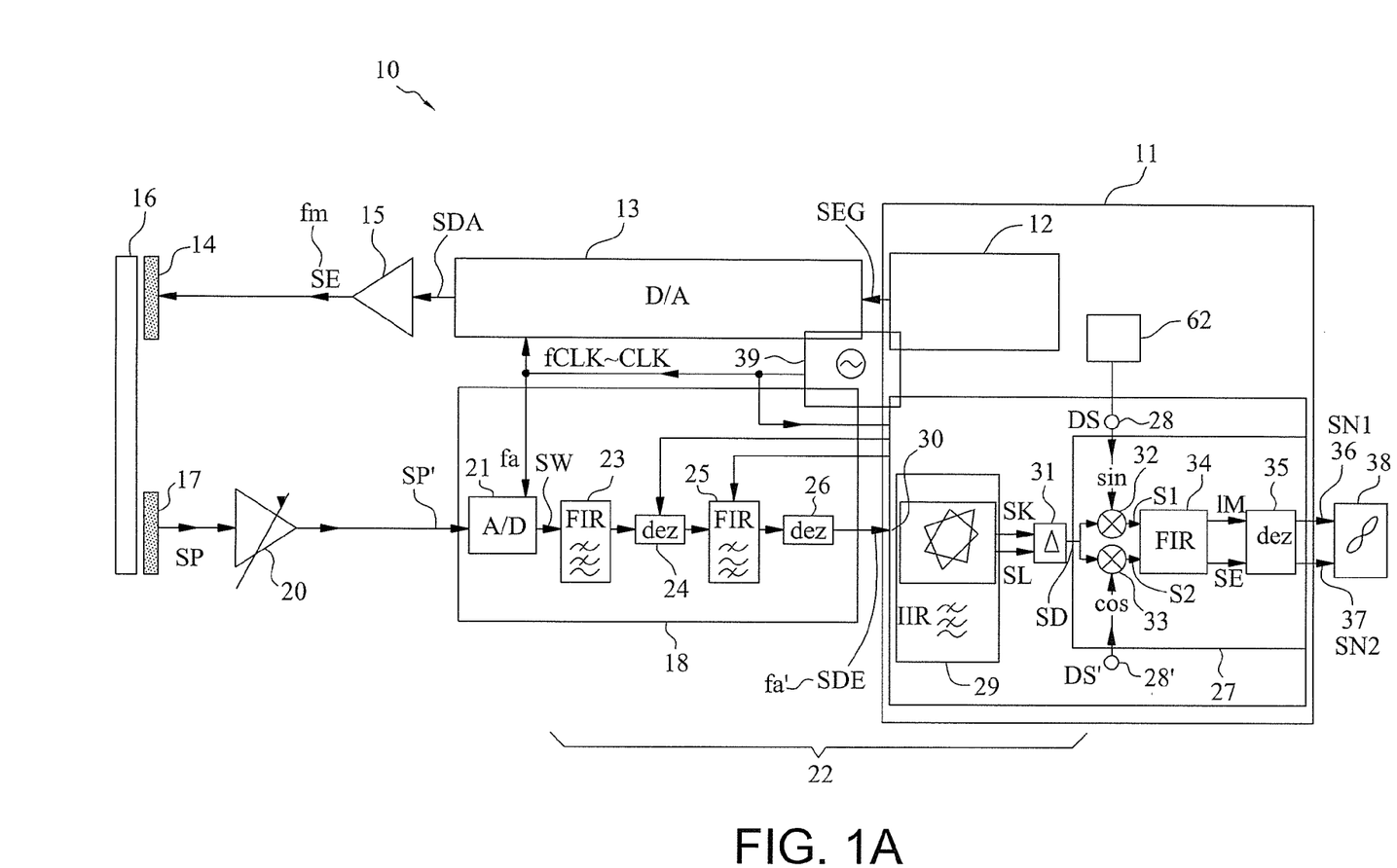
FIGS. 1A to 1C show an exemplary embodiment of a test set-up.

FIG. 1A shows an exemplary embodiment of a test set-up 10. The test set-up 10 comprises a signal processor 11, which has a generator 12. Furthermore, the test set-up 10 comprises a digital-analog converter 13 and an excitation coil 14. An output of the generator 12 is connected to an input of the digital-analog converter 13. An output of the digital-analog converter 13 is coupled to the excitation coil 14. Furthermore, the test set-up 10 comprises an excitation amplifier 15 that is arranged between the output of the digital-analog converter 13 and the excitation coil 14. A device being tested 16 is arranged near the excitation coil 14. In addition, the test set-up 10 has a receiving coil 17 and an AD converter 21. The receiving coil 17 is implemented as an absolute coil. The test set-up 10 implements an absolute channel test method. The receiving coil 17 is located close to the device being tested 16. An output of the receiving coil 17 is coupled to an input of an AD converter 21. Furthermore, the test set-up 10 comprises a receiving amplifier 20, which couples the receiving coil 17 to the AD converter 21. An amplification factor of the receiving amplifier 20 can be set by the signal processor 11.

The test set-up 10 has a filter arrangement 22, which is downstream to the AD converter 21. The filter arrangement 22 comprises a low-pass filter 23, which is downstream to the AD converter 21. Furthermore, the filter arrangement 22 comprises a decimation unit 24, which is downstream to the low-pass filter 23. The filter arrangement 22 also has a band-pass filter 25. The band-pass filter 25 is connected to the decimation unit 24 on the input side. In addition, the filter arrangement 22 comprises another decimation unit 26, which is downstream to the band-pass filter 25. The filter arrangement 22 thus comprises two filters 23, 25 that are connected one behind the other. The filter arrangement 22 implements a band-pass function. In addition, the filter arrangement 22 implements a low-pass function.

Moreover, the filter arrangement 22 comprises an input filter 29. The test set-up 10 has a demodulator 27. The demodulator 27 is implemented as a digital demodulator. The input filter 29 is arranged between the band-pass filter 25 and the other decimation unit 26 and the demodulator 27. A signal input of the demodulator 27 is coupled to an output of the input filter 29. Furthermore, the filter arrangement 22 comprises a subtractor 31, which connects the input filter 29 to the demodulator 27.

The demodulator 27 comprises first and second multipliers 32, 33, which are connected to the signal input and two demodulator inputs 28, 28' of the demodulator 27. Furthermore, the demodulator 27 comprises a demodulator filter 34 and a demodulator decimation unit 35, which are downstream to the first and second multipliers 32, 33. Moreover, the test set-up 10 comprises a display 38, which is coupled to the demodulator 27 on the input side. The test set-up 10 comprises a clock generator 39. The clock generator 39 is coupled to a clock input of the signal processor 11, a clock input of the digital-analog converter 13, as well as a clock input of the AD converter 21.

The test set-up 10 comprises an analog-digital converter arrangement 18, abbreviated AD-converter arrangement. The AD-converter arrangement 18 comprises the AD converter 21 as well as a portion of the filter arrangement 22, The AD-converter arrangement 18 has the low-pass filter 23, the decimation unit 24, the band-pass filter 25, and the other decimation unit 26. The signal processer 11 comprises another part of the filter arrangement 22 and the demodulator 27. The signal processor 11 has the input filter 29 and the subtractor 31.

The clock generator 32 provides a clock signal CLK with a clock frequency CLK. The clock signal CLK is sent to the AD-converter arrangement 18, the digital-analog converter 13, and the signal processor 11. The clock signal CLK thus synchronizes the processes in the signal processor 11, the digital-analog converter 13, as well as the AD-converter arrangement 18. The generator 12 provides a generator signal SEG in the form of digital values. The digital-analog converter 13 generates a digital-analog-converter signal SDA from the generator signal SEG. The digital-analog-converter signal SDA is amplified by means of the excitation amplifier 15 and sent as an excitation signal SE to the excitation coil 14. The rate at which the generator signal SEG provides digital values to the digital-analog converter 13 can thus be at most equal to the clock frequency $f_{CLK}$. The values of the generator signal SEG produce a sine function. In this case, the values of the generator signal SEG are repeated after a number L of values. The excitation signal SE has an excitation frequency $f_m$. For the excitation frequency $f_m$, $f_{CLK}=L*f_m$ thus applies. L is an integer. The signal processor 11 is designed to select and to set a value of the excitation frequency $f_m$ from an amount of preset values of the excitation frequency $f_m$.

A coil signal SP can be picked up on the receiving coil 17. The coil signal SP is amplified by the receiving amplifier 20 and sent to the AD converter 22 as an amplified coil signal SP'. The AD converter arrangement 18 generates an input signal SDE from the coil signal SP or the amplified coil signal SP'. The input signal is a digital signal. To this end, the AD converter 21 converts the amplified coil signal SP' into a converter output signal SW. The AD converter 21 scans the amplified coil signal SP' at a converter scan frequency $f_a$. The converter scan frequency $f_a$ is equal to the clock frequency $f_{CLK}$ of the clock generator 31. The coil signal SP is scanned at constant intervals. The time interval between two scan times is $1/f_a$ and is constant. The converter scan frequency $f_a$ is independent of the value of the excitation frequency $f_m$ and also remains constant during a change of the excitation frequency $f_m$.

The filter arrangement 22 generates a demodulator input signal SD from the converter output signal SW. To this end, the converter output signal SW is filtered by means of the low-pass filter 23 and converted with respect to the scan frequencies by means of the decimation unit 24. The decimation unit 24 implements conversion of a high scan frequency to a low scan frequency, i.e., down-sampling. The thus generated signal is filtered by means of the band-pass filter 25 and converted again with respect to the scan frequency by means of the additional decimation unit 26.

The input signal SDE that is provided by the AD converter arrangement 18 thus has a scan frequency $f_{a'}$. The scan rate $f_{a'}$ of the input signal SDE is less than the converter scan rate $f_a$. In this case, the following holds true: $f_a=R_1*f_{a'}$, whereby $R_1$ is a first reduction factor. The first reduction factor $R_1$ is an integer or a rational number. In this case, $R_1>0$. The signal processor 11 controls the filter arrangement 22, in particular, the decimation unit 24 and the band-pass filter 25, via control lines. The input signal SDE reflects values that are generated at identical time intervals. The time interval between two values of the input signal SDE is $1/f_{n'}$. The time interval is constant.

The input signal SDE is sent to the input filter 29. The input filter 29 is implemented as a low-pass filter. The scan frequency $f_{a'}$ of the input signal SDE is selected in such a way that a first number M of values occurs in a second number N of periods of the excitation signal SE. The input filter 29 filters the input signal SDE in an in-phase manner. On the output side, the input filter 29 provides a short-term signal low-pass filter SK and a long-term signal low-pass filter SL by low-pass filtering with a short and/or long time constant. The short-term signal low-pass filter SK and the long-term signal low-pass filter SL are sent to the subtractor 31. The subtractor 31 provides, on the output side, a demodulator input signal SD, which is a function of a difference between the short-term signal low-pass filter SK and the long-term signal low-pass filter SE The demodulator input signal SD is fed to the demodulator 27.

The signal processor 11 provides two demodulator signals DS, DS' in the form of sine values or cosine values to the first and second multipliers 32, 33 via the demodulator inputs 28, 28'. The provision of the sine and cosine values by the signal processor 11 is done with the scan frequency $f_{a'}$ of the input signal SDE. In this case, the sine value and the cosine value, which are sent to the first and second multipliers 32, 33, form a sine oscillation or a cosine oscillation with the excitation frequency $f_m$. The plot of the sine values of the demodulator signal DS, which are sent to the first multiplier 32, thus corresponds to the phase response of the generator signal SEG provided by the generator 12. The demodulation frequency of the demodulator signal DS, DS' is thus the excitation frequency $f_m$. The first multiplier 32 multiplies the demodulator signal DS in the form of sine values with the demodulator input signal SD. However, the second multiplier 33 multiplies the othe demodulator signal DS' in the form of cosine values with the demodulator input signal SD. The first demodulator output signal S1 provided by the first multiplier 32 and the second demodulator output signal S2 provided by the second multiplier 33 are filtered by means of the demodulator filter 34 and the demodulator decimation unit 35 and reduced relative to the scan frequency and issued as first and second wanted signals SN1, SN2 to first and second wanted signal outputs 36, 37 of the demodulator 27. The first wanted signal SN1 reflects the imaginary portion, and the second wanted signal SN2 reflects the real portion of the wanted signal.

The first and second wanted signals SN1, SN2 are depicted as points on the display 38. In this case, an X coordinate of the point corresponds to the first wanted signal SN1, and a Y coordinate of the point corresponds to the second wanted signal SN2. If the device being tested 16 has a flaw, the values that occur after one another in time of the first and second wanted signals SN1, SN2 form a loop on the display 38. If the device being tested 16, however, does not have any flaws in the area of the transceiver coil 14, 17, the first and second wanted signals SN1, SN2 will generate points close to a coordinate origin on the display 38. The signal processor 11 implements the input filter 29, the subtractor 31, as well as the demodulator 27 by means of a software-implemented method. The signal processor 11 performs the method for processing the input signal SDE on-line. The low-pass filter 23, the band-pass filter 25, and the demodulator filter 34 are designed as finite impulse response filters, abbreviated FIR filters. The input filter 29 is implemented as an infinite impulse response filter, abbreviated IIR filter.

In an alternative embodiment of the filter arrangement 22 that is not shown, the low-pass filter 23 and the decimation unit 24 are integrated in a unit.

In an alternative embodiment of the filter arrangement 22 that is not shown, the band-pass filter 25 and the other decimation unit 26 are combined into one unit.

In an alternative embodiment, not shown, a frequency divider is arranged between the clock generator 39 and the AD converter 21, which divides the clock frequency $f_{CLK}$ with a whole factor L1. Thus, the following holds true: $f_{CLK}=f_a*L1$.

In an alternative embodiment, not shown, the filter arrangement 22 is divided into the AD converter arrangement 18 and the signal processor 11 in a different way.

In an alternative embodiment, not shown, the test set-up 10 comprises a filter component, which comprises at least one portion of the filter arrangement 22. The filter component can implement, for example, the input filter 29.

In an alternative embodiment, not shown, the test set-up 10 comprises an anti-aliasing filter, which is arranged between the receiving coil 17 and the input of the AD converter 22. The anti-aliasing filter is implemented as a receiving low-pas filter. The filter can be referred to as an anti-scan-interference filter.

Figure 1B:
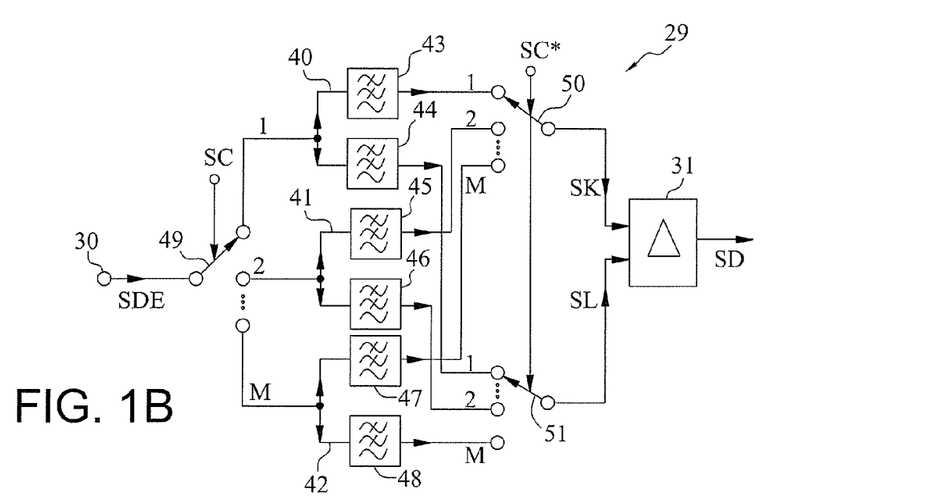

FIG. 1B shows an exemplary embodiment of the input filter 29, as it can be implemented in the test set-up 10 according to FIG. 1A. The input filter 29 comprises the first number M of low-pass filter arrangements 40, 41, 42. A first low-pass filter arrangement 40 comprises a first short-term low-pass filter 43 and a first long-term low-pass filter 44. A second low-pass filter arrangement 41 correspondingly comprises a second short-term low-pass filter and a second long-term low-pass filter 45, 46. Furthermore, the input filter 29 comprises additional short-term and long-term low-pass filters. Finally, an Mth low-pass filter arrangement 42 comprises an Mth short-term low-pass filter 47 and an Mth long-term low-pass filter 48. In addition, the input filter 29 comprises an input switch 49 as well as an output switch 50 and another output switch 51. The input switch 49 couples the filter input 30 of the input filter 29 alternately to the input of the first, the second, up to the Mth low-pass filter arrangement 40, 41, 42. The input of the first low-pass filter arrangement 40 is connected to the input of the first short-term low-pass filter 43 and the input of the first long-term low-pass filter 44. The equivalent applies for the second up to the Mth low-pass filter arrangement 41, 42.

The signal processor 11 controls the input switch 49 with a control signal SC in such a way that the first value of the first number M of values of the input signal SDE of the first low-pass filter arrangement 40 is sent to the second value of the second low-pass filter arrangement 41 as well as the Mth value of the Mth low-pass filter arrangement 42. The same is repeated with the next M values of the input signal SDE, i.e., in the following periods of the excitation signal SE. The short-term low-pass filters 43, 45, 47 filter the respective value of the input signal with a short time constant compared to a time constant of the long-term low-pass filters 44, 46, 48. The short-term low-pass filters 43, 45, 47 forward a first number Z1 of the periods of the excitation signal SE. However, the long-term low-pass filters 44, 46, 48 forward a second number Z2 of periods of the excitation signal SE. In this case, the following holds true: Z1<Z2.

The output switch 50 alternately switches an output of the first short-term low-pass filter 43, an output of the second short-term low-pass filter 45, and an output of the Mth short-term low-pass filter 47 to the first input of the subtractor 31. Synchronously, the additional output switch 51 alternately switches an output of the first long-term low-pass filter 44, an output of the second long-term low-pass filter 46, and an output of the Mth long-term low-pass filter 48 to the second input of the subtractor 31. At the output of the subtractor 31, the difference between the short-term signal low-pass filter SK and the long-term signal low-pass filter SL of the first low-pass filter arrangement 40 thus is present as the demodulator input signal SD, and then the difference between the two output signals of the second low-pass filter arrangement 41 up to the difference between the two output signals of the Mth low-pass filter arrangement 42 are available.

The input filter 29 thus implements a phase-separated low-pass filtering of the first number M of values of the input signal SDE. By the subtraction by means of the subtractor 31, the even component in each of the first number M of values of the input signal SDE is minimized, and only the alternating component is fed to the demodulator 27. Advantageously, very high noise suppression is achieved by means of the input filter 29 by the in-phase low-pass filtering of the first number M of values of the input signal SDE.

In an alternative embodiment, the input filter 29 is implemented as an FIR filter.

The input filter 29 can optionally also be designed for scan rate reduction. The short- and long-term low-pass filters 43 to 48 can produce a scan rate reduction.

Figure 1C:
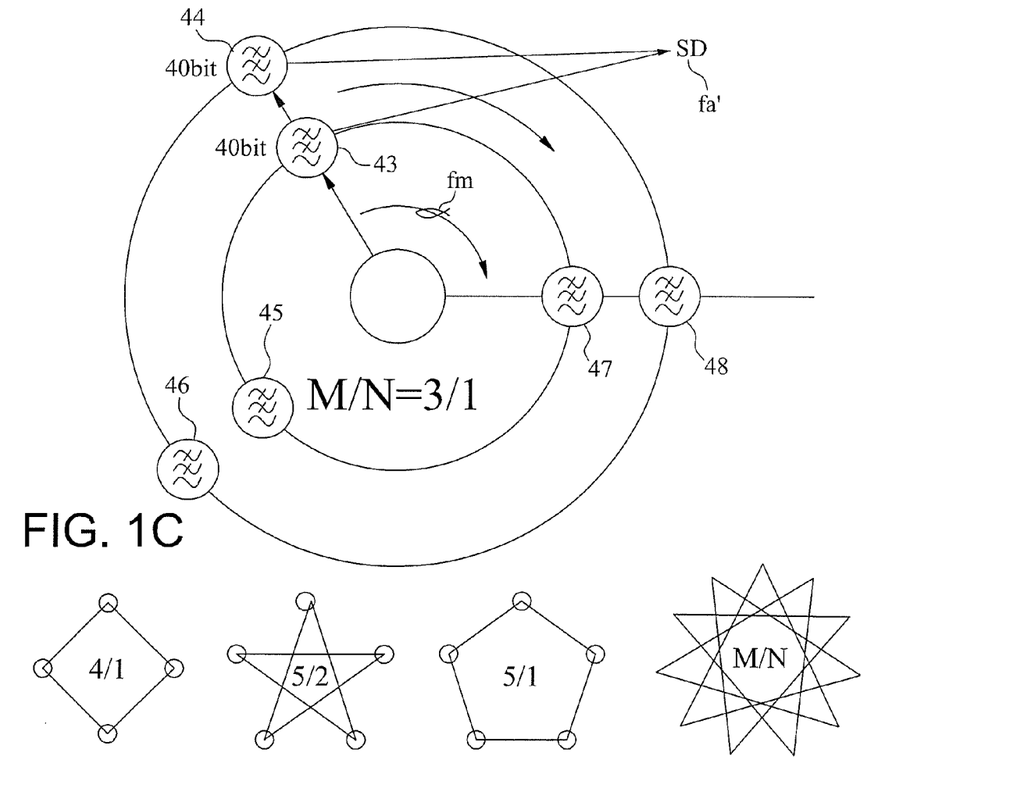

FIG. 1C shows a graphic depiction of the harmonic demodulation, as it is implemented by means of the input filter 29. The input signal SDE that is provided by the AD converter arrangement 18 is shown in magnitude and phase here. By way of example, in this connection, the relationships for a first number M=3 and a second number N=1 are shown. While the excitation signal SE runs through the second number N=1 period, the AD converter arrangement 18 provides the first number M=3 values of the input signal SDE. In this case, the first value of the first number M of values is sent both to the first short-term low-pass filter 43 and also to the first long-term low-pass filter 44. Accordingly, the second and third values of the first number M of values are sent to the second short-term and/or long-term low-pass filters 45, 46 of the second low-pass filter arrangement 41 or to the Mth short-term low-pass filter 47 and the Mth long-term low-pass filter 48 of the Mth low-pass filter arrangement 42. A short-term signal low-pass filter SK in the example at the output of the first short-term low-pass filter 43 can be calculated such that:

$$SK = SK' + SDE - \frac{SK'}{2^M},$$

whereby SK is the current value of the short-term signal low-pass filter, SK' is the previous value of the short-term signal low-pass filter, SDE is the current value of the input signal, and M is the first number.

The scan frquency $f_{a'}$ of the input signal SDE has a rational ratio to the excitation frequency fm. The rational ratio can be calculated according to the following equation:

$$f_{a'}=M/N \cdot f_m$$

By way of example, FIG. 1C depicts additional values for the rational ratio between the scan frequency $f_{a'}$ and the excitation frequency $f_m$.

A conventional digital demodulation can be performed using the following equations:

$$S1' = \frac{1}{n} \cdot \sum_n [SDE \cdot \sin(\omega t)] \text{ and}$$

$$S2' = \frac{1}{n} \cdot \sum_n [SDE \cdot \cos(\omega t)]$$

with $\omega = 2 \cdot f_m$

Primarily, however, the alternating component of the two signals S1', S2' is advantageous. The first signal S1, which reproduces the alternating components, can be calculated with the following equations:

$$S1 = \frac{1}{n1} \cdot \sum_{n1} [SDE \cdot \sin(\omega t)] - \frac{1}{n2} \cdot \sum_{n2} [SDE \cdot \sin(\omega t)] \text{ with } \omega = 2 \cdot f_m$$

In this case, the following holds true: n2>n1. For the first demodulator output signal S1 that is digitalized with the scan rate fa', the following is produced:

$$S1 = \frac{1}{n1} \cdot \left[\sum_{i=0}^{n1} \left(SDE_i \cdot \sin\frac{2 \cdot \pi \cdot fm \cdot i}{fa}\right)\right] - \frac{1}{n2} \cdot \left[\sum_{i=0}^{n2} \left(SDE_i \cdot \sin\frac{2 \cdot \pi \cdot fm \cdot i}{fa}\right)\right]$$

Since the scan frequency fa', also called sample frequency, for demodulation frequency, which is identical to the excitation frequency fm, is in a harmonic ratio, the first number M of angles is produced during the second number N of periods of the excitation signal SE. The following are produced with fa'*N=fm*M:

$$S1 = \frac{1}{n1} \cdot \left[\sum_{i=0}^{n1} \left(SDE_i \cdot \sin\frac{2 \cdot \pi \cdot N \cdot i}{M}\right)\right] - \frac{1}{n2} \cdot \left[\sum_{i=0}^{n2} \left(SDE_i \cdot \sin\frac{2 \cdot \pi \cdot N \cdot i}{M}\right)\right]$$

When addition is done over whole periods of the excitation signal SE, the angle factors can be written before the difference:

$$S1 = \sum_{n=1}^{N} \left[\sin\left(\frac{2 \cdot \pi}{n}\right) \cdot \left(\sum_{z=0}^{Z1} SDE_{z,n} - \sum_{z=0}^{Z2} SDE_{z,n}\right)\right]$$

$$\left(\sum_{z=0}^{Z1} SDE_{z,n} - \sum_{z=0}^{Z2} SDE_{z,n}\right) := \Delta_n$$

In this case, Z1 is a first number of periods and Z2 is a second number of periods of the excitation signal SE, over which averaging is done. $\Delta_n$ is the alternating component. Correspondingly, the second signal S2 is calculated by using the cosine function instead of the sine function.

The AD converter arrangement 18 performs the analog-digital conversion, for example, with 24-bit resolution. The low-pass filter arrangements 40, 41, 42 in the input filter 29 have, for example, an accuracy of 32 or 40 bits. The subtractor 31 is designed to scale the demodulator input signal SD to, for example, 16 bits. To process the alternating component $\Delta_n$ in the demodulator 27, a computational accuracy of, for example, 16 bits, is adequate. The demodulator 27 calculates the real and imaginary portions of the first and second signals S1, S2, and it implements post-filtering of the real and imaginary portions for generating the wanted signals SN1, SN2.

Because of the rational ratio M/N between the scan rate fa' and the excitation frequency fm, the scan frequency fa' can advantageously be matched to the excitation frequency fm. The excitation frequency fm can be converted between preset values during operation. The rational ratio M/N is set as a function of the value of the excitation frequency fm. The rational ratio M/N is reduced with an increasing value of the excitation frequency fm. The rational ratio M/N is set in such a way that the scan frequency fa' is smaller han a maximum scan rate that can be processed by the signal processor 11. In this case, the rational ratio M/N is set in such a way that the interval between the scan frequency fa' and the maximum scan frequency that can be processed by the signal processor 11 is as small as possible.

Advantageously, a table 62 in the signal processor 11, which contains the first number M of sine values and cosine values, is adequate for the storage of the demodulator signals DS, DS' at an excitation frequency fm. Also, for several preset values of the excitation frequency fm, the storage requirement for the table 62 in the signal processor 11 is low. The test set-up 10 implements a harmonic demodulation. The harmonic demodulation with sliding mean value formation makes it possible for a signal processor 11 that is designed for low processing speeds to be adequate for the signal processing. In the signal processor 11, only multiplications with sine/cosine table values and simple computation operations are performed.

Figure 2:
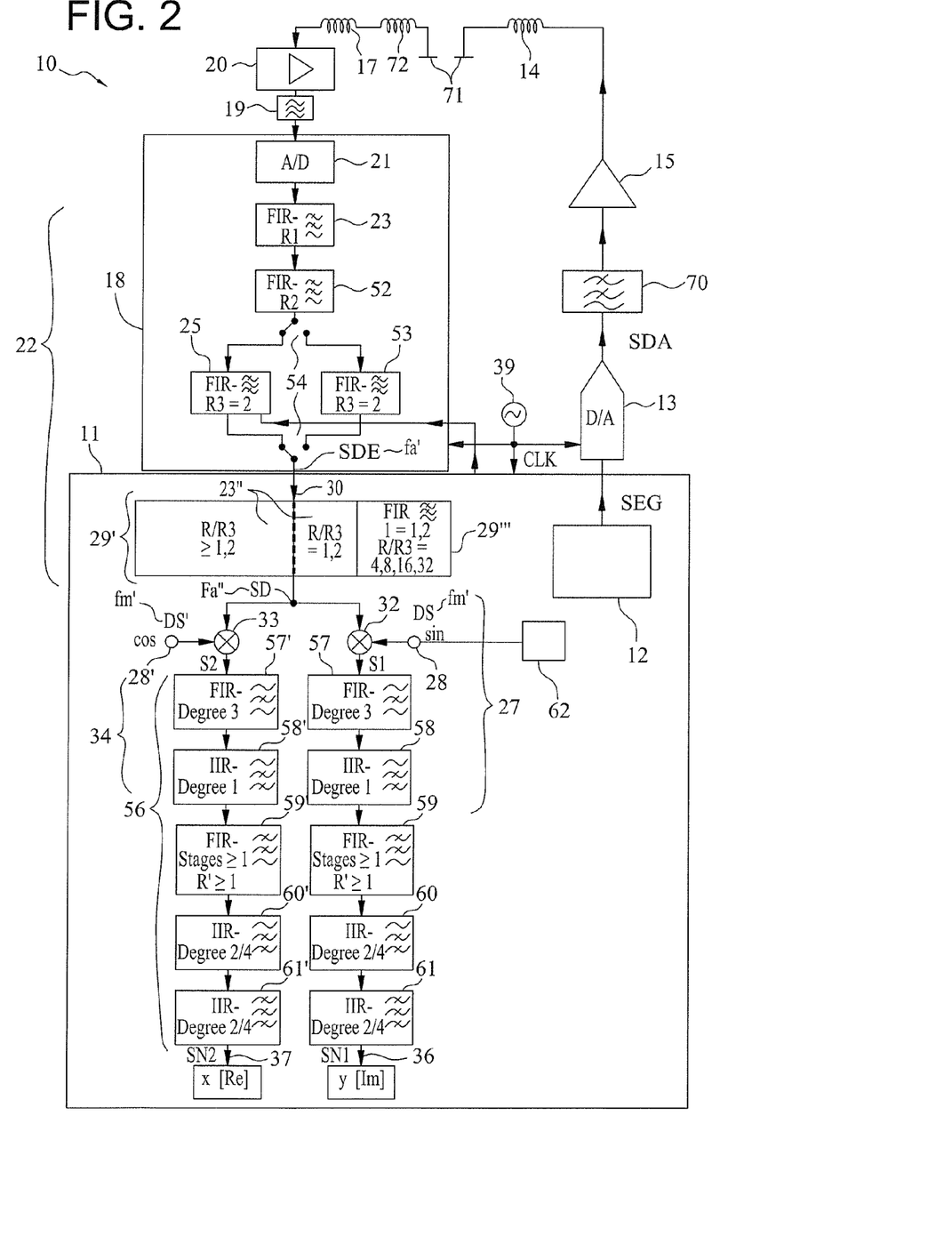
FIG. 2 shows another exemplary embodiment of a test set-up.

FIG. 2 shows another exemplary embodiment of the test set-up 10, which is a further development of the test set-up shown in FIG. 1A. The test set-up 10 comprises an excitation low-pass filter 70, which is arranged between the digital-analog converter 13 and the amplifier 15. The excitation signal SE is designed as a current that flows through the coil 14 to a reference potential connection 71. The receiving coil 17 is arranged between the reference potential connection 71 and the input of the receiving amplifier 20. Another receiving coil 72 of the test set-up 10 is arranged in series with the receiving coil 17. The receiving coil 17 and the additional receiving coils 72 thus form a differential coil arrangement. A series connection, comprising the receiving coil 17 and the additional receiving coil 72, couples an input of the receiving amplifier 20 to the reference potential connection 71. The test set-up 10 thus implements a differential channel test method. The receiving amplifier 20 thus ensures pre-amplification. An anti-aliasing filter 19 of the test set-up 10 couples the receiving amplifier 20 to the AD converter 21. The anti-aliasing filter 19 is implemented as a receiving low-pass filter. The amplified coil signal SP' is thus generated from the coil signal SP by amplification by means of the receiving amplifier 20 and by filtering by means of the anti-aliasing filter 19.

The filter arrangement 22 comprises a signal processing system 29'. The signal processing system 29' is arranged at the position of the input filter 29 that is depicted in FIG. 1A. The signal processing system 29' couples the band-pass filter 25 to the demodulator 27. The signal processing system 29' has a conversion system 29''. The conversion system 29'' is designed to provide only one value as the demodulator input signal SD to the scan frequency reduction of a first number P of values of the input signal SDE. In this case, the first number P is an integer and is greater than or equal to 1. In one embodiment, the first number P is greater than 1 . The signal processing system 29' performs this at high and mean values of the excitation frequency fm.

The signal processing system 29' is adjustable. If the excitation frequency fm has a low value, the signal processing system 29' activates a signal low-pass filter 29''. The signal processor 11 thus performs different method steps for signal processing of the input signal SDE depending on the value of the excitation frequency fm. While at high and mean values of the excitation frequency fm of P values, only one value of the input signal SDE is passed on, at low values of the excitation frequency fm, the input signal SDE is low-pass-filtered with an FIR characteristic 29'''. The signal processing system thus comprises the conversion system 29'' for high and mean excitation frequencies fm and the signal low-pass filter 29''' for low excitation frequencies fm.

The filter arrangement 22 has an additional low-pass filter 52, which is downstream of the low-pass filter 23. Furthermore, the filter arrangement 22 has an output low-pass filter 53 as well as a switch device 54. The switch device 54 switches either the band-pass filter 25 or the output low-pass filter 53 between the additional low-pass filter 52 and the signal processing system 29'. The band-pass filter 25 ensures signal band limitation before demodulation.

The demodulator filter 34 comprises two filter ladders 55, 56 that are separated from one another. A first filter ladder 55 couples the output of the first multiplier 32 to the first wanted signal output 36 of the demodulator 27. However, a second filter ladder 56 couples the output of the second multiplier 33 to the second wanted signal output 37 of the demodulator 27. The first and the second filter ladders 55, 56 are implemented identically.

The signal processing system 29' has an accuracy of 32 bits. The demodulator 27 is designed for a 32-bit accuracy. The word length in the demodulator 27 is 32 bits. The sine table that is used in the demodulator 27 is 16 bits long. The first filter ladder 55 has a band-rejection filter 57. The band-rejection filter 57 is downstream to the first multiplier 33. A high-pass filter 58, a low-pass filter 59, another high-pass filter 60 as well as another low-pass filter 61 are downstream to the band-rejection filter 57. The band-rejection filter 57 and the low-pass filter 59 are implemented as FIR (Finite Impulse Response) filters. The high-pass filters 58, 60 as well as the additional low-pass filter 61 are implemented as IIR (Infinite Impulse Response) filters. The first wanted signal SN1 indicates the imaginary portion, and the second wanted signal SN2 indicates the real portion of the wanted signal.

The demodulation method is implemented in a purely digital manner. The site of the digitalization is advantageously made the focal point as much as possible at the beginning of the signal processing ladder. This results in a savings of expensive analog circuits. Directly after the pre-amplification of the coil signal SP and after the anti-aliasing filter 19, the analog-digital conversion takes place in the AD converter 21. The anti-aliasing filter 19 can also be referred to as a receiving low-pass filter. The parameters of the anti-aliasing filter 19 are rigidly set. Since the conversion scan frequency fa is constant, the limiting frequency of the receiving low-pass filter 19 can be constant and also is not changed in an alteration of the excitation frequency fm. The AD convertor 21 can be implemented as a sigma-delta converter. In an exemplary embodiment, the AD converter arrangement 18 is implemented by means of the component AD7760 of Analog Devices. With the AD converter arrangement 18, the quantization as well as up to three FIR filter stages 23, 52, 25 or 23, 52, 53 that are connected behind one another are implemented for band limitation and scan frequency reduction. The filter stages are adjustable. The band-pass filter 25 or the output low-pass filter 53 is freely programmable by downloads of at most 96 coefficients.

The signal processor 11 performs the complex sine/cosine demodulation and the additional signal processing. The digital input signal SDE is real-valued and requires only a signal path. The analog circuit expense is reduced to one-half compared to a real-valued and imaginary-valued digital input signal. Advantageously, because of the few necessary components, a savings in cost and a very compact structure are made possible. Moreover, digital antecedents in comparison to analog circuits have a higher accuracy and are subject to smaller fluctuations.

The band-pass 25 can have, for example, the following values: converter scan rate $f_a$=5000 kHz, pass-band frequencies of 980 kHz to 1020 kHz, stop-band frequencies of 750 kHz to 1250 kHz, pass-band fluctuation 0.1 (-dB), stop-band fluctuation 120 (-dB), filter length 96, 32-bit floating point calculation, FIR (equiripple) design. Advantageously, the narrow band limitation and the high attenuation in suppressed band in the band-pass 25 produce a dynamic gain by reduction of noise and high noise immunity. Superpositions of outer band-interfering signals by folding are advantageously suppressed after the scan rate reduction.

The signal processor 11 generates the excitation frequency fm and the demodulation frequency of the demodulation signals DS, DS' from the clock signal CLK. The excitation frequency $f_m$, the demodulation frequency of the demodulation signals DS, DS' and the scan frequency $f_a$ of the AD converter 21 are synchronous to one another and are set exactly. The demodulation frequency is the frequency with which the sine and cosine values are provided to the demodulator 27. Thus, advantageously, no beats occur. Also, the clock signal CLK, the excitation signal SE, as well as a trigger signal of the AD converter 21, which has the converter scan rate $f_a$, are synchronous to one another. The excitation signal SE has a phase offset. With the phase offset, the running time in the filter arrangement 22 is compensated, so that no phase rotation is present between the demodulator input signal SD and the demodulator signal DS, DS'.

To generate the excitation signal SE with the excitation frequency $f_m$, the direct digital synthesis method, abbreviated DDS method, is used with a sine table and phase accumulator. In a table with $2^{2M1}$ entries of SinTab and a phase accumulator with N1-bit word width, sine values with the clock frequency $f_{CLK}$ are output according to the following equations:

$$\sin\left(2\pi \cdot \frac{fm}{fCLK} \cdot i\right) = \text{SinTab}[a_i \cdot 2^{-(N1-M1)}],$$

$$\text{SinTab}[i] = \sin\left(\frac{2\pi}{2^{M1}} \cdot i\right) \text{ with } i = 0, 1, \ldots, 2^{M1} - 1,$$

$$a_i = (i \cdot n) \bmod 2^{N1},$$

$$a_0 = 0$$

$$a_{i+1} = (a_i + n) \bmod 2^{N1} \text{ with } i = 0, 1, \ldots, N1 \text{ und } N1 \geq M1,$$

$$n = \frac{fm}{fCLK} \cdot 2^{N1}$$

In this case, n is the phase increment. The length of the sine table does not have any effect on the frequency accuracy, which by itself is fixed by the accumulator word width N1 and is $f_{CLK}/2^{N1}$. If n is a whole multiple of $2^{N1-M1}$, the output table values correspond exactly to the scan times of the desired sine function. As a deviation, because of the discrete amplitude stages, a quantization noise with the standard deviations s for rounded table values and a signal-to-noise ratio SNR are produced according to the following equation:

$$s = \frac{2^{-b}}{\sqrt{12}}$$

And $$SNR = 20 \cdot \log\left(\sqrt{\frac{3}{2}} \cdot 2^b\right) = 6 \cdot b + 1.8 \text{ [dB]}$$

whereby the table word width b is in bits. In all other values of n, the cutting of the non-integer table indices $[a_i * 2^{-(N1-M1)}]$ results in a phase error, which produces an additional noise component in the output in the form of an amplitude error that is modulated with the excitation frequency fm. For small phase errors ep, the following are produced for the digital-analog-converter signal SDA of the digital-analog converter 13:

$$\sin\left[2\pi \cdot \frac{fm}{fCLK} \cdot i + ep(i)\right] = \sin\left[2\pi \cdot \frac{fm}{fCLK} \cdot i\right] + ep(i) \cdot \cos\left[2\pi \cdot \frac{fm}{fCLK} \cdot i\right]$$

Because of the periodicity of the deviation, the error signal in this case has a discrete line spectrum. As an estimate of the distance between the maximum heights of all possible spectral lines of the phase error and the sine amplitude, the following holds true for any n in good approximation of the spurious-free dynamic range SFDR:

SFDR=6·M1−4 [dB]

Another special case with discrete spectral proportions is obtained when the excitation frequency fm of the sinusoidal excitation signal SE is a subharmonic of the clock frequency $f_{CLK}$, i.e., $f_{CLK}$ is a whole multiple of fm. Then, the energy of the quantization error is divided into a few spectral lines of the harmonics of the excitation frequency fm with considerably higher amplitudes than the theoretical value for equally-dispersed noise. To avoid later intermodulation interference, additional discrete frequency proportions should be as small as possible.

For a 14-bit digital-analog converter 13, a 16k table with $2^{14}$ entries with 14-bit word length is adequate. The amplitude-quantization noise is then −86 dB and with the presence of phase noise, the maximum spectral line of the error signal is at most −80 dB relative to the sine amplitude. Thus, only a single rigid analog excitation low-pass filter 70 is required as a reconstruction low-pass filter; a rigid clock frequency $f_{CLK}$ is used. To ensure the synchronicity and to reduce the circuit expense for the excitation low-pass filter 70, the 20 MHz clock of the AD converter 21 is also used as a clock signal CLK with the clock frequency $f_{CLK}$. With a maximum excitation frequency of fm=1 MHz and an attenuation in suppressed band of 60 dB in the half clock frequency $f_{CLK}/2$, a degree 3 excitation low-pass filter 70 with an edge steepness of 18 dB/octave is suitable. By the high scan rate of the digital-analog converter 13, in addition a low maximum amplitude deviation is also achieved because of the step function and the weighting G according to the following equation:

$$G = \sin\left(\frac{\pi \cdot fm}{fCLK}\right) \bigg/ \frac{\pi \cdot fm}{fCLK}$$

The deviation is −0.04 dB for the ratio $f_{CLK}/fm$=20. Taking into consideration the described requirements and criteria when selecting a decimal-geometric gradation with a factor of $Q=10^{1/k}$, the result of 1, 1.3, 1.6, 2, 2.5, 3.2, 4, 5, 6.3, 8, 10, which represents a third gradation, and thus a table with a total of 41 excitation frequencies fm in the required range of 100 Hz to 1 MHz, is produced for k=10 values per decade. In this case, the excitation frequency fm and the demodulation frequency are exactly identical. Advantageously, the expense for the tables and filters is low. For the individual frequencies, in each case the values are used that lie closest to the exact numerical values $Q^{i-1}$. Thus, the necessary resolution is also achieved at the low frequencies; the phase accumulator in the generator 12 has a word width of 32 bits. While no phase error occurs in the upper frequency range of the excitation frequency fm of 1 MHz to 16 kHz, at the low frequencies, it is reduced below 4 kHz of the entire signal-to-noise ratio to approximately 67 dB as a result of the phase noise. In the demodulation, because of the narrow band limitation, higher-frequency interference is all the more strongly suppressed the lower the excitation frequency fm is. At the frequencies 312 kHz, 20 kHz, 10 kHz and 5 kHz with integer ratio fa'/fm, the spectral lines of the harmonics are under a level of −100 dB because of the high overscanning. In an integer ratio $f_a/f_m$, the clock frequency $f_{CLK}$ is a whole multiple of the excitation frequency $f_m$.

As a result of the coil error voltage, the demodulation also produces a frequency component in the double demodulation frequency fm' in addition to the even component, and said demodulation frequency fm' is suppressed by the degree 3 linear-phase FIR band-rejection filter 57, 57' with only four coefficients. An accuracy of 16 bits for the coefficients is advantageously adequate.

Also, in the demodulation, 16-bit sine/cosine table values are used, since the additional spectral component thus generated is below −120 dB at the basic frequency. The use of Table 62 is faster than a calculation of the sine and cosine values. In a longer table 62, a finer setting of the demodulation frequency is possible, for example, 800 kHz with 69/256. With the subsequent degree 1 recursive high-pass filter 58, 58', the even component that is produced by the coil error voltage is suppressed. The band-rejection filter 57, 57' is located before the high-pass filter 58, 58', since otherwise, because of the high amplitude of the basic frequency harmonic, only very slow attenuated step responses would be the result. The high-pass filter 58, 58' is advantageously implemented as an IIR filter, since its limiting frequency and thus the transient response time can be switched very simply.

For error voltage suppression, a limiting frequency of 0.01 Hz is used. This corresponds to a minimum test speed of approximately 1.5 cm/minute with a 3 mm coil active width. At the scan frequency of $f_a$=833 kHz, this low limiting frequency can be produced with just about 32-bit coefficient accuracy. With 16-bit coefficients, only a limiting frequency of greater than 10 to 20 Hz is possible. The transient response time is approximately 36 s. For a quick adjustment, called quick balance, the coefficients are switched so that the high-pass filter 58, 58' has a limiting frequency of 10 kHz and a transient response time of 37 μs. The degree 1 IIR-high-pass filter 58, 58' makes possible an error voltage suppression with quick adjustment. The IIR filter type allows for a coefficient switch-over with the shortest transient response behavior, since a minimum phase system is present. Based on the degree 1, the computing expense is low.

The band-rejection filter 57, 57' is designed for suppression of a signal component at the double demodulation frequency. The error voltage can be suppressed by the IIR high-pass filter 58, 58'.

While up to this point of the signal processing, 32-bit arithmetic is required in the signal processor 11 for all numerical operations, the accuracy of the signal values can be reduced from 32 bits to 16 bits after the separation of the even component for the additional low-frequency signal processing. Since all 32-bit operations are performed with the reduced scan frequency $f_{a'}$ of at most 833 kHz, a relatively low computing time requirement consequently also follows for this method.

For further suppression of interference and residual folding components, the low-frequency wanted signal is limited by a single-stage or multi-stage FIR-low-pass filter 59, 59' with a total reduction factor R'≥1 to the presettable maximum band width $f_{MAX}$ at an overscanning $f_{a'}$=(20 . . . 100) $f_{MAX}$. At a minimum value of 20*$f_{MAX}$, it is just about ensured that amplitude errors of at most 1.5% are not exceeded for the signal analysis and production. If it is possible because of the test speed, an attempt is made to achieve the scan Frequency 100*$f_{MAX}$. Advantageously, a more compact sequence of the scan points for the graphic depiction is thus achieved. The largest possible amplitude error is then less than 0.1%.

An even higher overscanning does not offer any advantages and, because of the redundancy, results in an unnecessary increase in the data yield and the storage requirement. Since usually the device being tested 16 is moved past the receiver coil 17, the signal processor 11 has to analyze the data of the input signal SDE online to make possible a localization of the error in the device being tested 16. For the example of the excitation frequency $f_m$=1 MHz, the FIR low-pass filter 59, 59' with 23 coefficients and a band limitation to 15 kHz follows as a post-filter. In this connection, the scan frequency is reduced to 208 kHz. In addition to an effective suppression of optional interfering signals and removal of residual intermediate frequency components, the low-pass filter 59, 59' is used in addition to correct the damping of the degree 3 band-rejection filter 57, 57' in the pass-band range.

A very high damping of the frequency component in the double demodulation frequency is generated by the zero point of the FIR band-rejection filter 57, 57' and the post-filtering in the following reduction low-pass filter 59, 59'. FIR filters can be used very efficiently for scan rate reduction. Because of the finite impulse response, the calculation at the scan frequency $f_{a'}$ or the reduced scan frequency fa" is possible. FIR filters have a linear phase, so that distortions are avoided, and the time signal shape is maintained. By the narrow-band filtering, the wanted signal band can lie closer to the excitation frequency fm, specifically, for example, up to a factor of 3 below the excitation frequency fm (and thus no longer has to be at least less than 1/10 of the excitation frequency fm). The narrow-band filtering produces high noise immunity and a reduction of noise.

The number of computing operations relative to the input scan rate of 833 kHz is 5.75 16-bit multiplications and 5.75 additions. Overall, approximately 76 operations in one microsecond are required so far per input scan interval for real and imaginary portions. Finally, in each case, an IIR high-pass filter 60, 60' and a degree 2 or 4 IIR-low-pass filter 61, 61' follows the reduction low-pass filter 59. The IIR high-pass filter 60, 60' and the IIR low-pass filter 61, 61' are recursive filters and are rigidly set.

Figure 3A:
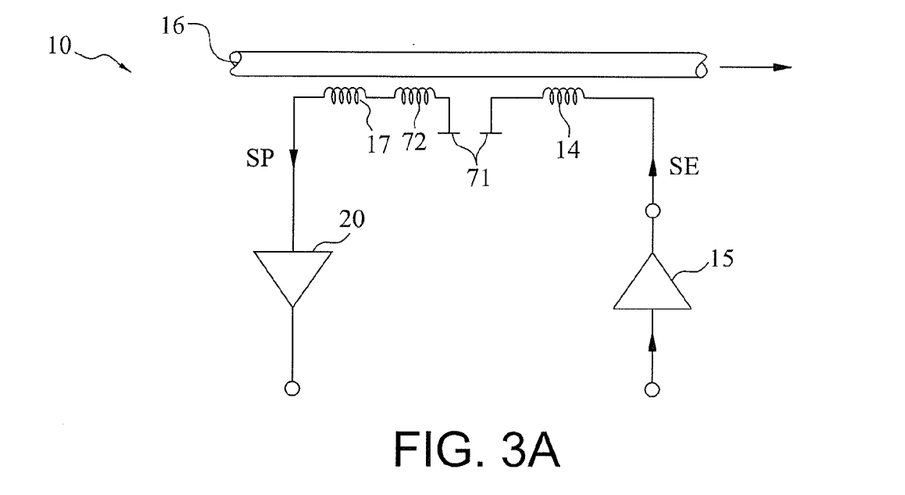
FIGS. 3A and 3B show exemplary embodiments of details of a test set-up.

As an alternative, the IIR high-pass filter 60, 60' and the IIR low-pass filter 61, 61', which are both recursive filters, are automatically readjusted as a function of the test speed. In this case, because of the large frequency range, optionally coefficients with 32-bit word lengths may be necessary. Thus, the IIR high-pass filter 60, 60' and the IIR low-pass filter 61, 61' are automatically matched by the test set-up 10 to the test speed, with which the device being tested 16 is examined. To this end, the coefficients of the filters 60, 60', 61, 61' are calculated and switched by the signal processor 11. The IIR high-pass filter 60, 60' and the IIR low-pass filter 61, 61' produce a filtering of the low-frequency wanted signal for noise suppression. The IIR high-pass filter 58, 58' is used primarily in a differential coil arrangement, as shown in FIG. 3A. If only one coil, namely the receiving coil 17, is used on the receiving side, the test set-up 10 implements an absolute channel. In the case of an absolute channel, the bias-IIR-high-pass filter 58, 58' is replaced by a subtractor, which subtracts a compensation value from the signal. The compensation value for the zero adjustment is determined and readjusted by the signal processor 11.

In the filter arrangement 22, the low-pass filter 23 has a scan rate reduction by a factor of 4, and the band-pass filter 25 and the output low-pass filter 53 in each case have a scan rate reduction by a factor of 2. A scan rate reduction factor of the other low-pass filter 52 can be set. The clock frequency fCLK is typically 20 MHz and is used both by the AD converter arrangement 18 and by the generator 12.

In an alternative embodiment, a 10 MHz clock is used as a scan rate for reducing the load of the signal processor 11 for the digital generation of the excitation signal SE with the excitation frequency fm instead of 20 MHz. As a result, the phase increment is increased. Because of the step function, the maximum amplitude deviation is then −0.14 dB. The excitation filter 70, which is used as a reconstruction filter, can then have a degree of 5 to 6 with an edge steepness of 30 to 36 dB per octave.

In an alternative embodiment, the signal processor 11 calculates the sine and cosine values of the demodulator signal DS, DS'. The calculation can be done by series approximation or by means of the CORDIC (COordinate Rotation DIgital Computer) method.

FIG. 3A shows an exemplary embodiment of a detail of the test set-up 10 as it can be used, for example, in the test setup according to FIG. 1A. The additional receiving coil 72 of the test set-up 10 is arranged in series in the receiving coil 17. The receiving coil 17 and the additional receiving coil 72 thus form a differential coil arrangement.

Figure 3B:
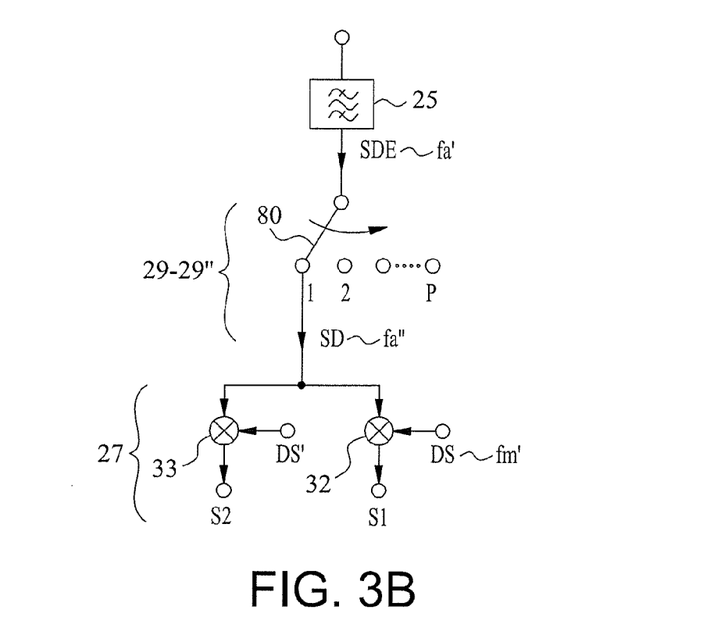

FIG. 3B shows an exemplary embodiment of another detail of the test set-up 10 according to FIG. 2. The test setup 10 has the band-pass 25 and the demodulator 27, between which the signal processing system 29' is provided. Below, the signal processing system 29' is explained for high values of the excitation frequency fm, in which the conversion system 29" is activated. The conversion system 29" is used for scan rate reduction.

The conversion system 29" is implemented as a switch 80. An input of the switch 80 is connected to the band-pass filter 25. The switch 80 has the first number P of outputs. Finally, the first output of the switch 80 is connected to the demodulator 27. The conversion system 29" reduces the scan frequency $f_{a'}$ by the whole factor of P to the reduced scan frequency $f_{a''}$. The conversion system 29" can therefore also be referred to as a downward mixer. The conversion system 29" is implemented as a decimator. It can also be referred to as a resampler. The conversion system 29" is thus implemented in that only each Pth value is transmitted. The intermediate values are omitted. The signal processor 11 implements the conversion system 29" and the demodulator 27 by storage and further processing by means of demodulation of each Pth value of the input signal SDE. The signal processor 11 receives the unnecessary P−1 value of the input signal SDE but does not demodulate the latter.

The signal processing system 29' implements a conversion method using the conversion system 29". Advantageously, the conversion method does not require any explicit multiplication by changing the scan frequency $f_{a'}$ to the reduced scan frequency fa". The operations in the signal processing system 29' and the subsequent operations are implemented by the signal processor 11 with the reduced scan frequency $f_{a''}$. Thus, there is a savings in computing time. A signal processor 11 can be used at low speed.

Advantageously, the AD conversion, filtering and scan rate reduction and subsequent demodulation are carried out with observance of the sampling theorem and the folding properties of time-discrete systems and with use of aliasing. A rational ratio between the scanning frequency $f_{a''}$ and the mean frequency fm is not necessary. The method can also be implemented without a rational ratio between the scan frequency $f_{a'}$, $f_{a''}$ and the excitation frequency $f_m$.

Figure 4A:
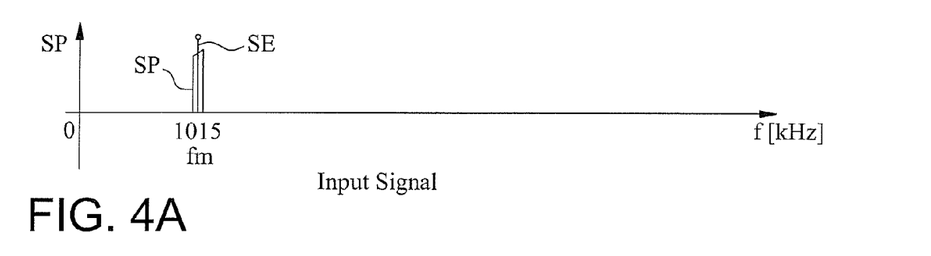
FIGS. 4A to 4D show an exemplary view of frequency spectra occurring in a test set-up.
Figure 4B:
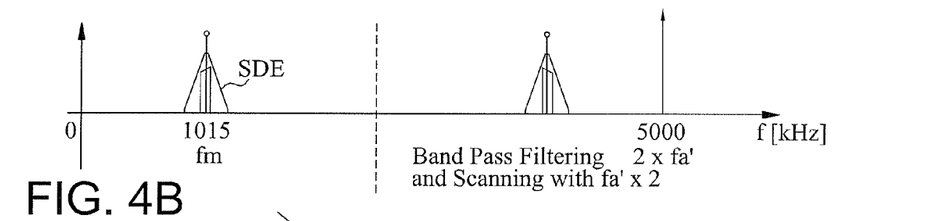
Figure 4C:
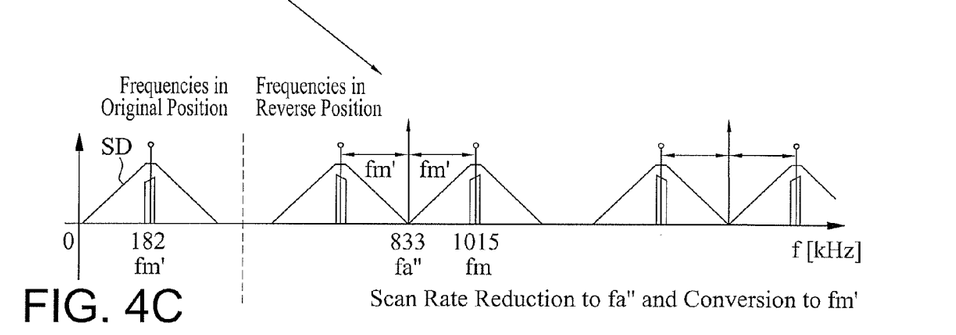
Figure 4D:
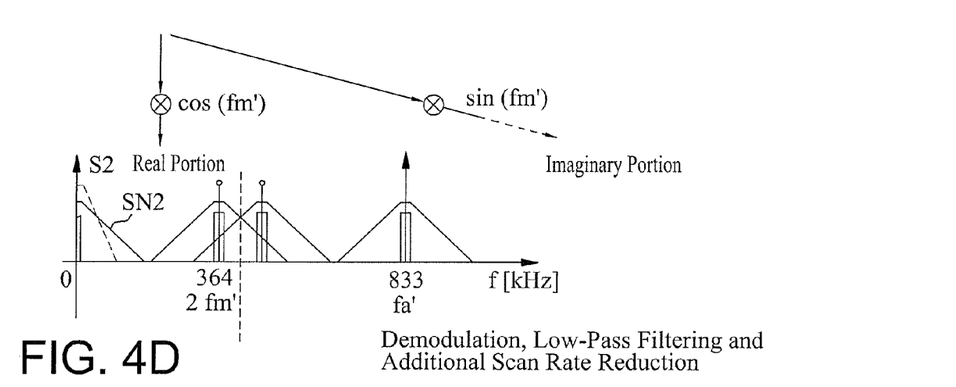

FIGS. 4A to 4D show an exemplary embodiment of the spectra in the test set-up 10 according to FIG. 3B. In the example, the excitation frequency fm has the value of 1015 kHz. In FIG. 4A, the frequency spectrum of the coil signal SP is indicated. FIG. 4B shows the input signal SDE after scanning with the converter scan rate fa and the band-pass filtering by means of the band-pass filter 25. FIG. 4C shows the rate-reduced demodulator input signal SD that is provided by the conversion system 29" of the signal processing system 29'. The scan frequency fa' in this case, is scan-rate-reduced to the reduced scan frequency $f_{a''}$, and the excitation frequency $f_m$ is converted to a demodulation frequency after conversion $f_{m'}$. The demodulation frequency after conversion fm' can also be referred to as an intermediate frequency. In FIG. 4D, the first and second wanted signals SN1, SN2 are indicated, which are generated by demodulation, low-pass filtering, and additional scan rate reduction within the demodulator 27.

The coil signal SP is narrow-banded and amplitude- and phase-modulated. The coil signal has a bandwidth of 15 kHz in this example. The scan frequency of the AD converter arrangement 18 is $f_a=5$ MHz. The band-pass filter 25 has a band-pass range of +/−15 kHz and a band-rejection limit of +/−170 kHz to the band limitation. The conversion system 29" reduces the scan frequency fa' by a factor of 6 to fa"=833 kHz. The scan rate reduction factor is thus 6. The coil signal SP is thus converted, i.e., mixed downward to the intermediate frequency fm' according to the following equation:

$$fm' = (fm) \bmod fa'' = \frac{7}{32} \cdot fa'' = 182 \text{ kHz}$$

This is the modulo demodulation method. With the method of frequency conversion by downward mixing, the filtered signal of the band-pass filter 25 is converted to a lower intermediate frequency. This is suitable primarily for high excitation frequencies fm. For low excitation frequencies fm, however, the signal of the band-pass filter 25 is directly demodulated after low-pass filtering by means of the signal low-pass filter 29'''.

By reduction of the scan frequency fa' by a factor of R to the reduced scan frequency fa"=fa'/R, the excitation frequency fm is depicted on the intermediate frequency fm'=(fm)mod fa". The demodulation can be carried out in the original position or in the reverse position of the frequency. As a requirement of the original position of the spectrum at fm', the following has to hold true:

$$k \cdot f_{a''} < f_m < (k+0.5) \cdot f_{a''}$$

where K is an integer. This corresponds to the requirement $f_{m'} < f_{a''}/2$. Thus, no reverse position of the frequency takes place. In addition, the condition has to be met:

$$f_b < f_{m'} < f_{a''}/2 - f_B$$

The symmetry of the spectrum is thus maintained, and the real-valued nature of the corresponding time function is proven effective. The band-pass signal at fm' is then complex-demodulated with $\sin(2\pi \text{ fm'} t)$ and $\cos(2\pi \text{ fm'} t)$. The intermediate frequency fm', the reduced scan frequency $f_{a''}$, and thus the scan frequency $f_{a'}$ are in a harmonic ratio to one another. This means that the reduced scan rate fa" is a rational multiple of the intermediate frequency m'. Furthermore, $f_{m'}/f_{a''}=a/b$ holds true, whereby a and b are integers. As a result, it is achieved that during demodulation, a small table length for the sine-/cosine function value is adequate. The reduction factor R is a multiple of R3=2 and is therefore even-numbered. The input data rate in the signal processor 11 is $f_a/2$ times 32-bit and is 2.5 M samples at $f_a=5$ MHz, which are 5 Mword/s at 16 bits. In a blackfin processor as a signal processor 11, the largest possible data rate for a 16-bit word length is approximately 50 M word/s. For R>2, in each case only the scan values in a ratio R/2 are further used. All other read-in values are ignored. Thus, the demodulation frequency $f_{m'}$ is unlike the excitation frequency $f_m$. However, at lower frequencies without downward mixing, the demodulation frequency is equal to the excitation frequency $f_m$.

The method can thus have the following advantages: A complete digital demodulation and filtering is carried out. In addition, a band-pass filtering is carried out in the AD-converter arrangement 18. The operations are performed on the intermediate frequency at a lower scan frequency. Thus, there is a savings in computing time. The use of a processor at low speed is made possible. Only an AD converter 21 and a signal path are required between the receiver coil 17 up to the demodulator 27 for demodulation of real and imaginary portions, i.e., in-phase/quadrature components, on the intermediate frequency. By contrast, in general two AD converters are required in the case of conventional underscanning with direct demodulation and conversion into the base band. The test set-up 10 performs the test method online. The test set-up 10 can be implemented economically.

What is claimed is:

1. Test set-up for non-destructive detection of a flaw in a device being tested by means of an eddy current, comprising:
    an excitation coil adapted to act on a device being tested with an alternating electromagnetic field,
    a receiving coil adapted to generate a coil signal as a function of a flaw in the device being tested,
    an analog-digital converter having an input side which is coupled to the receiving coil,
    a filter arrangement having an input side which is coupled to an output side of the analog-digital converter and is adapted for band-pass filtering and scan frequency reduction, and
    a demodulator having an input which is coupled to an output of the filter arrangement
    wherein the filter arrangement comprises a band-pass filter, an input of which is coupled to the analog-digital converter and an output of which is coupled to the demodulator to issue an input signal, and
    wherein the filter arrangement further comprises a conversion system that is adapted to provide only one value as the demodulator input signal for scan frequency reduction of a first number of values of the input signal, whereby the first number is an integer greater than 1.

2. Test set-up according to claim 1, wherein the analog-digital converter is adapted to produce a converter output signal with a converter scan frequency; wherein the filter arrangement is adapted to convert a converter output signal into a demodulator input signal having a reduced scan frequency which is smaller than the converter scan frequency by a reduction factor, and wherein the demodulator is adapted to demodulate the demodulator input signal.

3. Test set-up according to claim 1 wherein the analog-digital converter is adapted to provide an input signal having a first number of values during a second number of periods of the excitation signal, the first number and the second number being different integers, wherein the filter arrangement comprises a number of low-pass filter arrangements and wherein each of the values of the input signal is sent to a respective one of the low-pass filter arrangements.

4. Test set-up according to claim 3, in which at least one of the low-pass filter arrangements comprises a short-term low-pass filter and a long-term low-pass filter which has a longer time constant compared to a time constant of the short-term low-pass filter.

5. Test set-up according to claim 1, further comprising a band-rejection filter, an input of which is coupled to the demodulator.

6. Test set-up according to claim 1, further comprising a signal processor, a generator that is coupled to the excitation coil and comprises the demodulator, the generator being adapted to issue a demodulator signal to a demodulator input of the demodulator.

7. Test set-up according to claim 6, further comprising a digital-analog converter which is arranged between the generator and the excitation coil.

8. Test set-up according to claim 6, further comprising a clock generator the output of which is coupled to a clock input of the signal processor and a clock input of the analog-digital converter.

9. Test method for non-destructive detection of a flaw in a device being tested by means of an eddy current, comprising the steps of:
  acting on the device being tested with an electromagnetic alternating field by means of an excitation coil to which an excitation signal is sent,
  generating a coil signal as a function of a flaw in the device being tested by means of a receiving coil,
  providing a converter output signal by digitalization of the coil signal,
  generating a demodulator input signal by filtering the converter output signal with a band-pass characteristic and scan frequency reduction, and
  demodulation of the demodulator input signal by by means of a demodulator,
  wherein the converter output signal is provided with a converter scan frequency and the demodulator input signal is provided with a reduced scan frequency which is smaller than the converter csan frequency by a reduction factor.

10. Test method for non-destructive detection of a flaw in a device being tested by means of an eddy current, comprising the steps of:
  acting on the device being tested with an electromagnetic alternating field by means of an excitation coil to which an excitation signal is sent,
  generating a coil signal as a function of a flaw in the device being tested by means of a receiving coil,
  providing a converter output signal by digitalization of the coil signal,
  generating a demodulator input signal by filtering the converter output signal with a band-pass characteristic and scan frequency fate reduction, and
  demodulation of the demodulator input signal by means of a demodulator,
  wherein the input signal is generated by means of a band-pass filter from the converter output signal or a signal derived from the converter output signal; and wherein a scan frequency reduction by a first number that is an integter greater than 1 is produced from values of the input signal, and wherein only one value is provided as the demodulator input signal.

11. Test method according to claim 10 wherein a scan frequency of the input signal is a rational multiple of an excitation frequency of the excitation signal, and wherein the input signal has a first number of values during a second number of periods of the excitation signal, the first number and the second number being different integers.

\* \* \* \* \*